United States Patent [19]

Benardella

[11] Patent Number: Plant 6,568

[45] Date of Patent: Jan. 31, 1989

[54] ROSE PLANT NAMED BENDAY

[75] Inventor: Frank A. Benardella, Old Tappen, N.J.

[73] Assignee: Nor'East Miniature Roses, Inc., Rowley, Mass.

[21] Appl. No.: 62,066

[22] Filed: Jun. 15, 1987

[51] Int. Cl.[4] ..... A01H 5/00

[52] U.S. Cl. ..... Plt./9

[58] Field of Search ..... Plt./9

*Primary Examiner*—Robert E. Bagwill
*Attorney, Agent, or Firm*—Vincent G. Gioia

[57] ABSTRACT

A new unusual Cardinal red miniature rose variety.

1 Drawing Sheet

The present invention relates to a new and distinct variety of rose plant of the miniature rose class, which was originated by my crossing as seed parent the rose known as "Rise 'N Shine" (U.S. Plant Pat. No. 4,231) and as pollen parent the rose known as "Harmonie". The denomination of this new rose is "Benday".

Among the novel characteristics possessed by this new variety which distinguish it from its parents and all other varieties of which I am aware are its unusual Cardinal red flowers of excellent exhibition hybrid tea-like form. Asexual reproduction by budding of the new variety as performed in San Bernardino County, Calif. shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "53B" is plate 53B of The Royal Horticultural Society Colour Chart.

Parentage: Seedling.
*Seed parent.*—"Rise 'N Shine".
*Pollen parent.*—"Harmonie".
Class: Miniature.

The following observations are made of specimens grown outdoors in San Bernardino County, Calif. during the month of April.

FLOWER

Blooming habit: Recurrent.

A. Bud:
(1) *Size.*—Medium.
(2) *Form.*—Long pointed.
(3) *Color.*—As sepals separate, bud color is near 53B.
(4) *Sepals.*—Slightly longer than bud.
(5) *Peduncle.*—Length — about 1⅜ inch. Aspect — straight. Strength — erect. Color — near 146D.

B. Bloom:
(1) *Size.*—Average size when fully expanded — about 2 inches.

(2) *Borne.*—Singly, one to a stem and several together in sprays.
(3) *Form.*—Flowers high centered at first, becoming flat. Outer petals with pointed apices reflex and quill to points; then petals roll under.
(4) *Petalage.*—Number of petals under normal conditions — about 23–25.
(5) *Color.*—After sepals fall and petals unfurl. flowers are well formed exhibition style and of Cardinal red coloring near 53B to 53D. Petals are yellow colored at point of petal attachment.

C. Petals:
(1) *Texture.*—Medium.
(2) *Appearance.*—Inside velvety and outside satiny.
(3) *Form.*—Fan shaped.
(4) *Arrangement.*—Regularly arranged.
(5) *Petaloids in center: Few.*
(6) *Persistence.*—Drop off cleanly.
(7) *Fragrance.*—Slight to none.
(8) *Lasting quality.*—Average.

REPRODUCTIVE ORGANS

A. Stamens, filaments and anthers:
*Arrangement and color.*—Regularly arranged around styles. Color — filaments near 20A.

B. Pollen:
*Color.*—Near 20D.

C. Styles: Medium, uneven.

D. Stigmas:
*Color.*—Near 2C.

E. Hips: None observed.

PLANT

A. Form: Upright.

B. Growth: Very Vigorous.
*Height attained.*—About 16–20 inches.

C. Foliage: Compound 5 to 7 leaflets.
(1) *Size.*—Medium.
(2) *Quantity.*—Average.
(3) *Color.*—New foliage: Upper side — near 146A. Under side — near 184B. Old foliage: Upper side — near 139A. Under side — near to 148C.
(4) *Shape.*—Oval, pointed.
(5) *Texture.*—Upper side is semiglossy: under side is matte.
(6) *Edge.*—Serrate.
(7) *Serration.*—Ordinary.
(8) *Leaf stem.*—Color — near to 133C. Under side — near 146B.
(9) *Stipules.*—Medium, not bearded.

(10) *Resistance to disease.*—Blackspot — Average. Mildew — Average. Rust — Average.

D. Wood:

(1) *New wood.*—Color — near 146B. Bark — smooth.

(2) *Old wood.*—Color — near 137B. Bark — smooth.

E. Thorns:

(1) *Thorns.*—Quantity (main stalk) — ordinary. On laterals from stalk — ordinary. Form — long, thin, curved slightly downward. Length — medium. Color — near 182C. Position — irregular.

(2) *Prickles.*—None.

F. Winter hardiness: Needs protection in severe climate.

I claim:

1. A new and distinct variety of rose plant of the miniature rose class, substantially as shown and described, characterized particularly by Cardinal red flowers of excellent exhibition form.

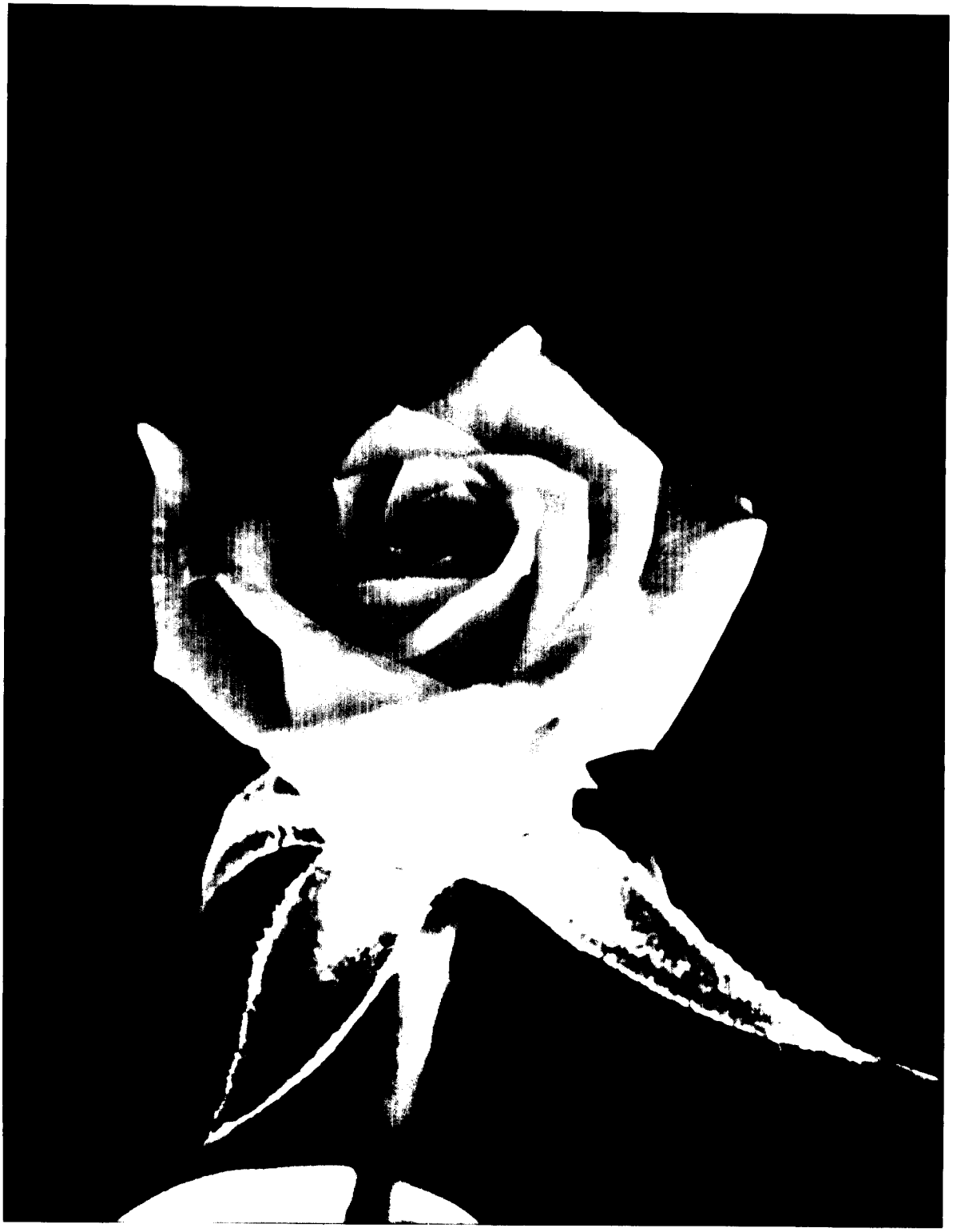

* * * * *